(12) United States Patent
Liu et al.

(10) Patent No.: US 8,859,113 B2
(45) Date of Patent: Oct. 14, 2014

(54) CARBAZOLE DERIVATIVES AND ORGANIC LIGHT-EMITTING DIODE DEVICE USING THE SAME

(71) Applicant: China Petrochemical Development Corporation, Taipei (TW)

(72) Inventors: Hsian Chan Liu, Kaohsiung (TW); Min Sheng Chen, Kaohsiung (TW); Chin Yi Lee, Chiayi (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 14/048,558

(22) Filed: Oct. 8, 2013

(65) Prior Publication Data
US 2014/0175400 A1    Jun. 26, 2014

Related U.S. Application Data

(63) Continuation of application No. 13/010,804, filed on Jan. 21, 2011, now Pat. No. 8,580,396.

(30) Foreign Application Priority Data

Aug. 16, 2010    (TW) .................................. 99127288

(51) Int. Cl.
*H01L 51/54*    (2006.01)
*H01L 51/00*    (2006.01)
(Continued)

(52) U.S. Cl.
CPC ........ *H01L 51/0061* (2013.01); *H01L 51/0069* (2013.01); *H05B 33/20* (2013.01); *H01L 52/0037* (2013.01); *H01L 51/0072* (2013.01);
(Continued)

(58) Field of Classification Search
USPC .................. 428/690, 917; 313/504, 505, 506; 564/26, 426, 433, 434; 546/18, 79, 81, 546/101; 257/40, E51.05, E51.026, 257/E51.032; 548/418, 440
See application file for complete search history.

(56) References Cited

U.S. PATENT DOCUMENTS

| 6,649,772 B2 | 11/2003 | Lin et al. |
| 2009/0045726 A1 | 2/2009 | Miki et al. |

FOREIGN PATENT DOCUMENTS

| CN | 1978441 A | 11/2005 |
| EP | 1972625 A1 | 11/2000 |

(Continued)

OTHER PUBLICATIONS

Benzimidazole/Amine-Based Compounds Capable of Ambipolar Transport for Application in Single-Layer Blue-Emitting OLEDs and as Hosts for Phosphorescent Emitters, Lai et al., Agnew. Chem. Int. Ed. 2008, vol. 47, pp. 581-585.

(Continued)

*Primary Examiner* — Gregory Clark
(74) *Attorney, Agent, or Firm* — Woodard, Emhardt, Moriarty, McNett & Henry LLP

(57) ABSTRACT

The present invention relates to novel carbazole derivatives and an organic light-emitting diode device using the same. These carbazole derivatives can simultaneously or singly be used as a hole transporting layer, a host or guest of an emitting layer or an electron transporting layer of an organic light-emitting diode device.

10 Claims, 1 Drawing Sheet

(51) Int. Cl.
  *H05B 33/20* (2006.01)
  *C09K 11/06* (2006.01)
  *C07D 403/10* (2006.01)
  *C07D 413/10* (2006.01)
  *H05B 33/14* (2006.01)
  *H01L 51/50* (2006.01)

(52) U.S. Cl.
  CPC ............ *C09K 11/06* (2013.01); *H01L 51/0085* (2013.01); *C07D 403/10* (2013.01); *H01L 51/0081* (2013.01); *C09K 2211/1033* (2013.01); *H01L 51/007* (2013.01); *C07D 413/10* (2013.01); *H01L 2251/308* (2013.01); *C09K 2211/1048* (2013.01); *H01L 51/5012* (2013.01); *H01L 51/0067* (2013.01); *H05B 33/14* (2013.01); *H01L 51/5048* (2013.01); *C09K 2211/1074* (2013.01); *Y10S 428/917* (2013.01)

USPC ........... 428/690; 428/917; 313/504; 313/505; 313/506; 257/E51.05; 257/E51.026; 257/E51.032; 564/26; 564/426; 564/433; 564/434; 546/18; 546/79; 546/81; 546/101; 548/418; 548/440

(56) References Cited

FOREIGN PATENT DOCUMENTS

| EP | 1661888 B1 | 11/2008 |
| JP | 2006/69962 | 3/2003 |
| TW | 1297038 | 11/2000 |
| WO | WO 2007069607 A1 | 6/2007 |

OTHER PUBLICATIONS

International Search Report, PCT/JP2006/324766.

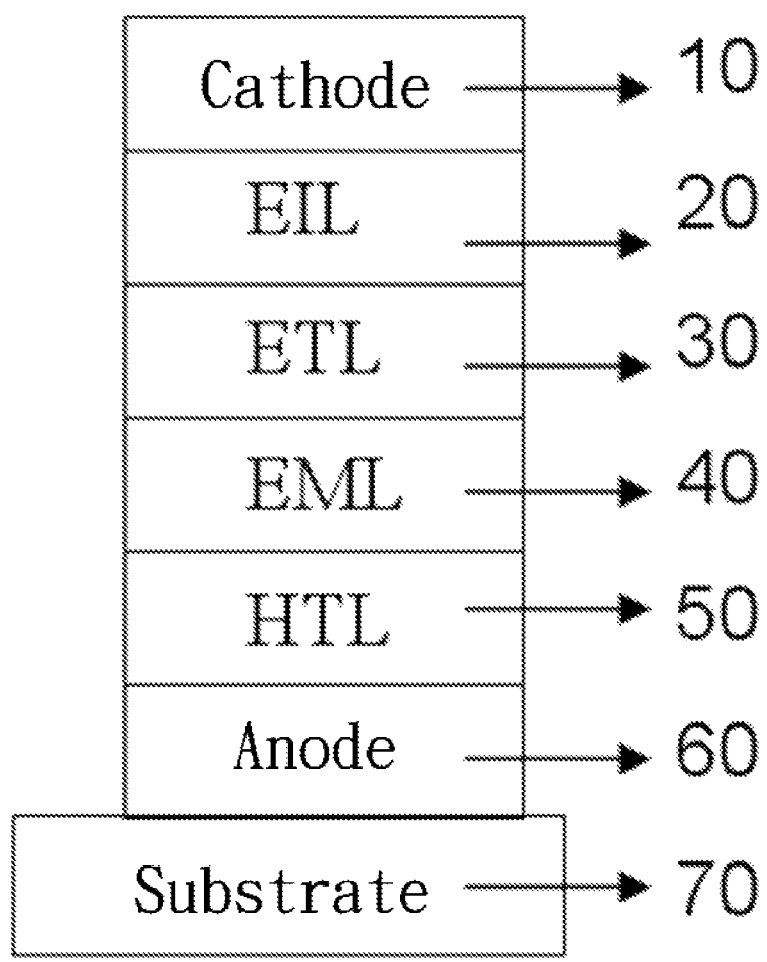

CARBAZOLE DERIVATIVES AND ORGANIC LIGHT-EMITTING DIODE DEVICE USING THE SAME

CROSS-REFERENCE TO RELATED APPLICATIONS

This application is a continuation of U.S. application Ser. No. 13/010,804 (pending), filed Jan. 21, 2011, which claims the benefit of Taiwan Application No. 099127288, filed Aug. 16, 2010, all of which are hereby incorporated by reference in their entirety.

FIELD OF THE INVENTION

The present invention relates to novel carbazole derivatives, which can be used as a hole transporting layer, a host or guest of an emitting layer, or an electron transporting layer of an organic light-emitting diode (OLED) device, and the organic light-emitting diode device using such carbazole derivatives.

BACKGROUND TO THE INVENTION

An OLED display is regarded as the next generation display as it has advantages such as self-luminescence, high contrast ratio, no viewing angle limitation, fast response time, etc. An OLED device comprises a cathode, an anode and organic layers, and the organic layers are composed of a hole transporting material, an electron transporting material and a light-emitting material. Carbazole derivatives have properties such as good planarity, high it bond conjugation, effective charge transfer, rigid structure that can increase the glass transition temperature of a material, etc., and are usually used as the materials for the hole transporting layer or the emitting layer of an OLED.

For example, CN 1978441 discloses a phenyl carbazole compound having excellent charge transfer ability can be used as the material for a hole injection layer, a hole transporting layer or an emitting layer. WO 2007/069607 discloses a carbazole compound that can be used in the host of a blue phosphorescent organic light-emitting diode. A film made by co-deposition of the material of said patent and FIrpic (iridium(III) bis(4,6-difluorophenylpyridinato)picolate) almost has a phosphor efficiency of 100%. JP 2006-69962 discloses a carbazole compound that can be used in the host of a green phosphorescent organic light-emitting diode device. TW 1297038 discloses a carbazole compound having a high glass transition temperature. In said patent, a carbazole material is used for the hole transporting layer and the emitting layer, TPBI (1,3,5-tris(N-phenylbenzimidazole-2-yl)benzene) is used for the electron transporting layer, and the luminescence efficiency of its device is 2.5 lm/W at 5 V. EP 1972625 discloses a series of materials having carbazole and oxadiazole structures, and the structural features of such compounds are that the third and sixth positions of the carbazole are hydrogen atoms or aliphatic functional groups. Said patent indicates that its materials are adapted to be used as a host of the emitting layer, which is, however, not demonstrated with real experimental data. *Angew. Chem. Int. Ed.* 2008, 47, 8104 mentions a carbazole compound adapted to be used as a host of a green phosphorescent organic light-emitting diode, and the efficiency of its device is up to 20.2%.

In the aforementioned prior art, the carbazole derivatives are widely used in the hole transporting layer and the emitting layer, and it has not been disclosed that carbazole derivatives are used as the materials for the electron transporting layer. In view of this, the present invention provides novel carbazole derivatives that can be used as the material for the electron transporting layer, and can be used as the hole transporting layer, the electron transporting layer and the emitting layer simultaneously, which can effectively simplify the procedure for manufacture of the devices.

SUMMARY OF THE INVENTION

The object of the present invention is to provide novel organic materials of carbazole derivatives and to apply them to an organic light-emitting diode device. FIG. 1 is a schematic diagram showing the structure of an OLED device. As shown in FIG. 1, the organic electroluminescence device mainly comprises an anode 60, an organic emitting layer (EML) 40 and a cathode 10. The anode 60 is constituted by coating a glass substrate 70 with a transparent conductive indium tin oxide (ITO) layer. The cathode 10 is a metal layer composed of, for example, aluminum (Al). A hole transporting layer (HTL) 50 is provided between the organic emitting layer 40 and the anode 60. An electron transporting layer (ETL) 30 and an electron injection layer (EIL) 20 are provided between the organic emitting layer 40 and the cathode 10.

Another object of the present invention is to provide an organic light-emitting diode device. In the said OLED device, the carbazole derivatives of the present invention are used as the organic materials for at least one of a host or guest of the emitting layer, the hole transporting layer and the electron transporting layer. In the example of application described later, the carbazole derivatives of the present invention are contained in an OLED device as the materials of at least one of the hole transporting layer, the host or guest of the emitting layer and the electron transporting layer.

The carbazole derivative according to the present invention has a structure represented by the formula (1):

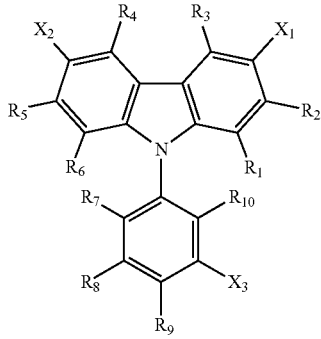

formula (1)

wherein $R_1$-$R_{10}$ are independently selected from the group consisting of hydrogen atom, OH, $NH_2$, $NO_2$, CN, $C_{1-6}$ alkoxyl group, $C_{1-10}$ alkyl group, $C_{1-20}$ fluorinated alkyl group, $C_{2-10}$ alkenyl group, $C_{2-10}$ alkynyl group, $C_{6-20}$ aryl group, $C_{6-20}$ fluorinated aryl group and $C_{4-20}$ heterocyclic aryl group, and $X_1$-$X_2$ are each any one structure selected from the group consisting of the structures represented by the formulae (2)-(4):

formula (2)
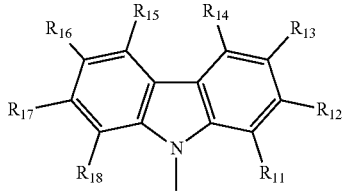

formula (3)
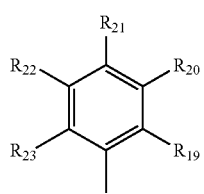

formula (4)
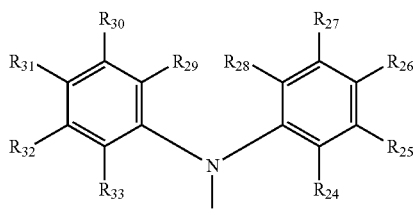

wherein $R_{11}$-$R_{33}$ are independently selected from the group consisting of hydrogen atom, OH, $NH_2$, $NO_2$, CN, $C_{1-6}$ alkoxyl group, $C_{1-10}$ alkyl group, $C_{1-20}$ fluorinated alkyl group, $C_{2-10}$ alkenyl group, $C_{2-10}$ alkynyl group, $C_{6-20}$ aryl group, $C_{6-20}$ fluorinated aryl group and $C_{4-20}$ heterocyclic aryl group, and $X_3$ is any one structure selected from the group consisting of the structures represented by the formulae (5)-(7):

formula (5)
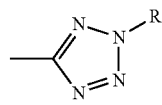

formula (6)

formula (7)
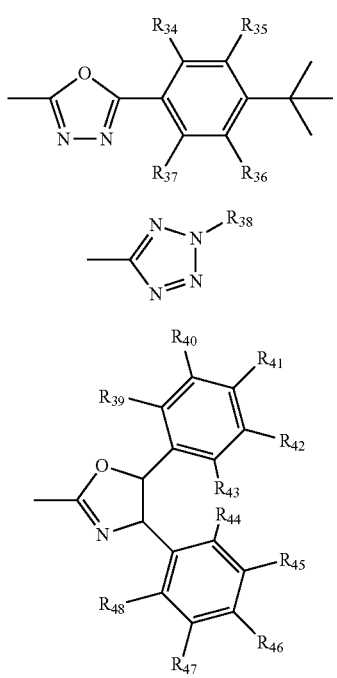

wherein $R_{34}$-$R_{37}$ and $R_{39}$-$R_{48}$ are independently selected from the group consisting of hydrogen atom, OH, $NH_2$, $NO_2$, CN, $C_{1-6}$ alkoxyl group, $C_{1-10}$ alkyl group, $C_{1-20}$ fluorinated alkyl group, $C_{2-10}$ alkenyl group, $C_{2-10}$ alkynyl group, $C_{6-20}$ aryl group, $C_{6-20}$ fluorinated aryl group and $C_{4-20}$ heterocyclic aryl group, and $R_{38}$ is selected from the group consisting of hydrogen atom, $C_{1-4}$ alkyl group and $C_{6-10}$ aryl group.

The synthesis of a series of carbazole derivatives according to the present invention and the test on the OLED devices to which the carbazole derivatives were applied will be described below in detail with reference to the following embodiments, and also as set forth in applicants' Taiwanese priority application No. 099127288, filed Aug. 16, 2010, the entire contents of which are hereby incorporated herein by reference. However, these embodiments are used mainly to assist in understanding the present invention, but not to restrict the scope of the present invention. Various possible modifications and alterations could be conceived of by one skilled in the art to the form and the content of any particular embodiment, without departing from the spirit and scope of the present invention, which is intended to be defined by the appended claims.

BRIEF DESCRIPTION OF THE DRAWINGS

FIG. 1 is a schematic diagram showing the structure of an OLED device.

DESCRIPTION OF PREFERRED EMBODIMENTS

According to the preferred embodiments of the present invention, a series of carbazole derivatives having the following structures are synthesized and then a test was conducted on the OLED devices to which they were applied.

The carbazole derivative has the following structure when $X_1$ and $X_2$ are carbazol groups and $X_3$ is a 5-(4-tert-butyl-phenyl)-1,3,4-oxadiazol group:

(Compound 1)
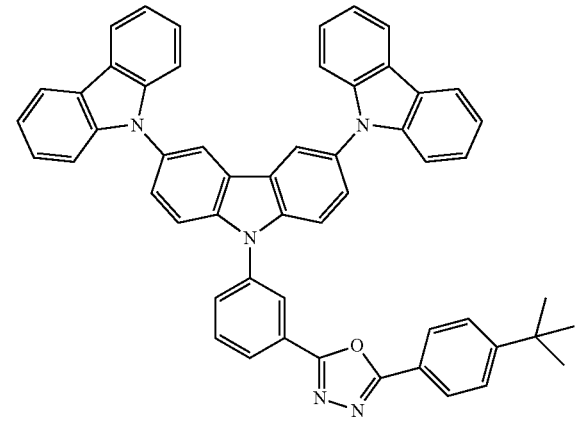

The carbazole derivative has the following structure when $X_1$ and $X_2$ are phenyl groups and $X_3$ is a 5-(4-tert-butyl-phenyl)-1,3,4-oxadiazol group:

(Compound 2)

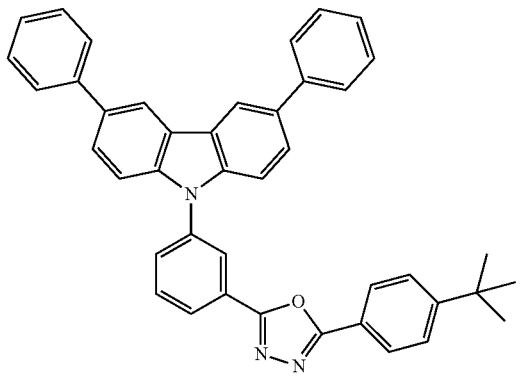

The carbazole derivative has the following structure when $X_1$ and $X_2$ are N,N-diphenylamino groups and $X_3$ is a 5-(4-tert-butyl-phenyl)-1,3,4-oxadiazol group:

(Compound 3)

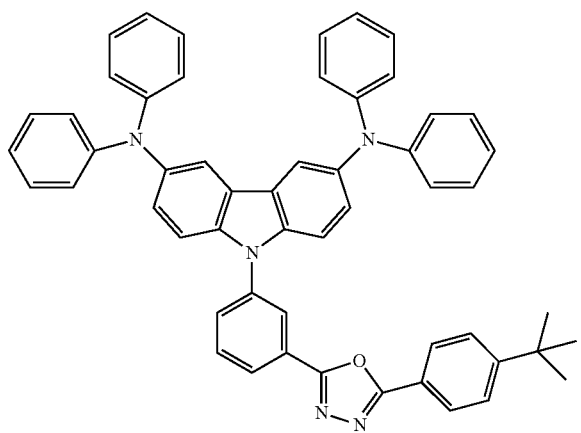

The carbazole derivative has the following structure when $X_1$ and $X_2$ are phenyl groups and $X_3$ is a 2-methyl-1H-tetraazol-5-yl group:

(Compound 4)

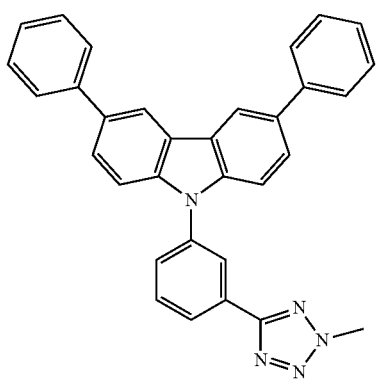

The carbazole derivative has the following structure when $X_1$ and $X_2$ are phenyl groups and $X_3$ is a 4,5-diphenyl-1,3-oxazol-2-yl group:

(Compound 5)

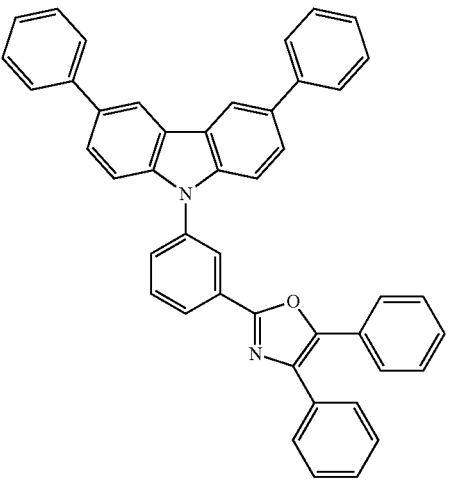

The method for synthesizing the carbazole derivatives according to the present invention is described in detail below.

(The Synthesis of Compound 1)

In a 250 ml two-neck flask, 80 ml of N,N-dimethyl formamide (DMF), 2.92 g (6.85 mmol) of 3-(3,6-dibromo-9H-carbazol-9-yl) benzonitrile, 0.98 g (15.08 mmol) of sodium azide ($NaN_3$), 0.81 g (15.08 mmol) of ammonium chloride ($NH_4Cl$), and a stir bar were added. The reaction was carried out with reflux under a nitrogen atmosphere for 24 hours. After the completion of reaction, 20 ml of 10% hydrochloric acid (HCl) was added and a filtering was conducted. The crude product was purified by column chromatography to obtain 3.21 g of a white solid product of 3,6-dibromo-9-(3-2H-tetraazol-5-yl-phenyl)-9H-carbazole (yield: 82.9%).

In a 50 ml two-neck flask, 2.5 g (5.33 mmol) of 3,6-dibromo-9-(3-2H-tetraazol-5-yl-phenyl)-9H-carbazole, 4.19 ml (21.45 mmol) of 4-tert-butylbenzoyl chloride, 3.5 ml of pyridine, and a stir bar were added. After the reaction was carried out with reflux under a nitrogen atmosphere for 8 hours, an extraction was conducted. The crude product was purified by column chromatography to obtain a white solid product of 3,6-dibromo-9-(3-(5-(4-tert-butyl-phenyl)-1,3,4-oxadiazol-2-yl)phenyl)-9H-carbazole (yield: 69.1%).

In a 250 ml two-neck flask, 75 ml of toluene, 0.15 g (0.62 mmol) of palladium acetate ($Pd(OAc)_2$) catalyst, 2.00 g (20.79 mmol) of sodium tert-butoxide ($NaO^tBu$), 50 ml (2.5 mmol) of Tri-tert-butylphosphine ($P^tBu_3$), 1.74 g (10.39 mmol) of carbazole, 2.5 g (4.16 mmol) of 3,6-dibromo-9-(3-(5-(4-tert-butyl-phenyl)-1,3,4-oxadiazol-2-yl)phenyl)-9H-carbazole, and a stir bar were added. The reaction was carried out with reflux for 30 hours. After the completion of reaction, 10% HCl was added and then an extraction was conducted with water and ethyl acetate (EA). The resultant organic layer was concentrated and then purified by column chromatography to obtain a white solid product (yield: 31.7%).

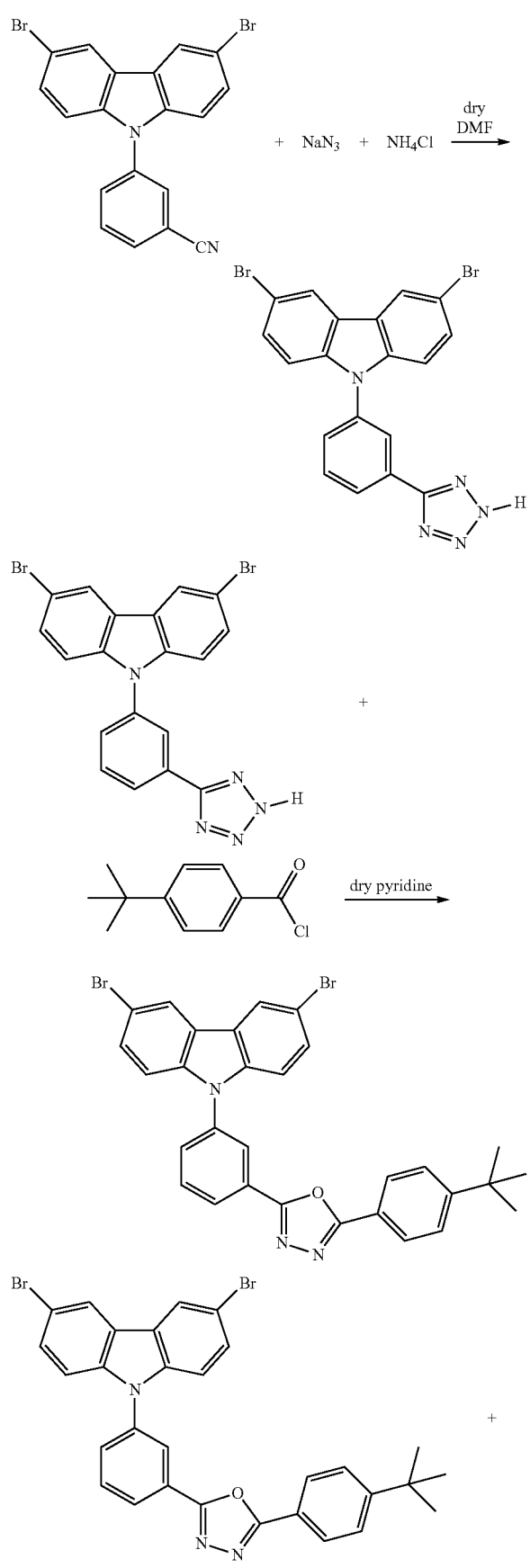
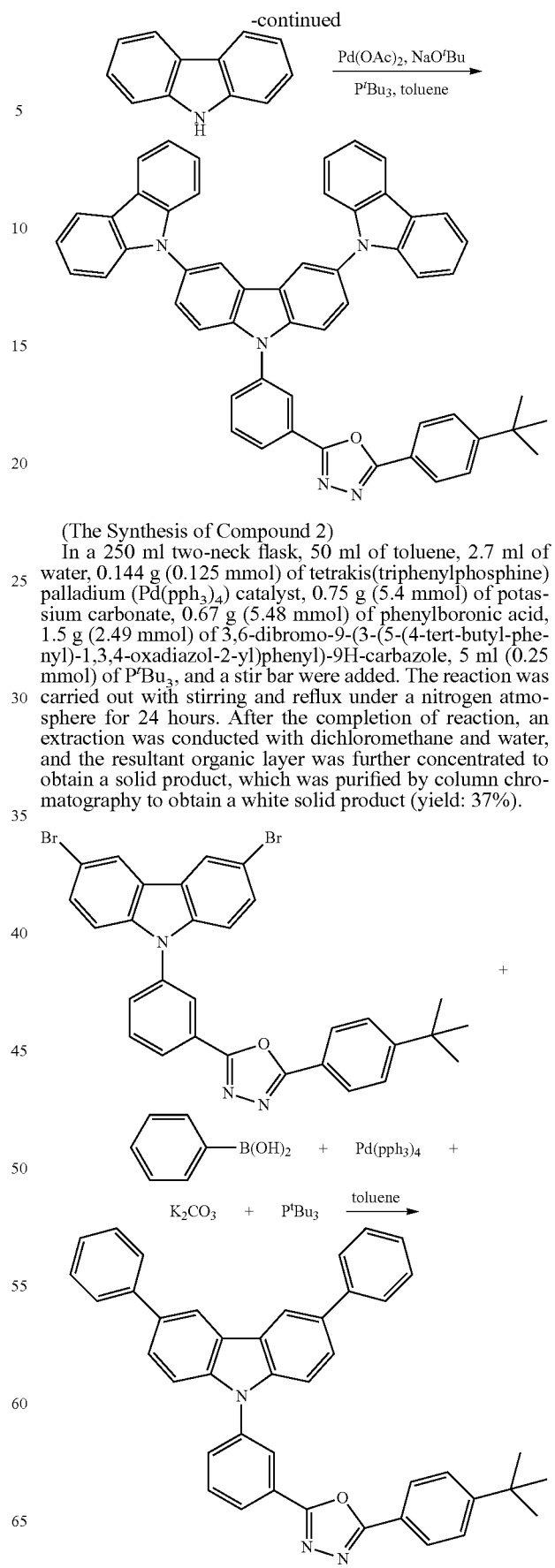

(The Synthesis of Compound 2)

In a 250 ml two-neck flask, 50 ml of toluene, 2.7 ml of water, 0.144 g (0.125 mmol) of tetrakis(triphenylphosphine) palladium (Pd(pph$_3$)$_4$) catalyst, 0.75 g (5.4 mmol) of potassium carbonate, 0.67 g (5.48 mmol) of phenylboronic acid, 1.5 g (2.49 mmol) of 3,6-dibromo-9-(3-(5-(4-tert-butyl-phenyl)-1,3,4-oxadiazol-2-yl)phenyl)-9H-carbazole, 5 ml (0.25 mmol) of P$^t$Bu$_3$, and a stir bar were added. The reaction was carried out with stirring and reflux under a nitrogen atmosphere for 24 hours. After the completion of reaction, an extraction was conducted with dichloromethane and water, and the resultant organic layer was further concentrated to obtain a solid product, which was purified by column chromatography to obtain a white solid product (yield: 37%).

(The Synthesis of Compound 3)

In a 250 ml two-neck flask, 75 ml of toluene, 0.15 g (0.62 mmol) of Pd(OAc)$_2$ catalyst, 2.00 g (20.79 mmol) of NaO$^t$Bu, 50 ml (2.5 mmol) of P$^t$Bu$_3$, 1.76 g (10.39 mmol) of diphenylamine, 2.5 g (4.16 mmol) of 3,6-dibromo-9-(3-(5-(4-tert-butyl-phenyl)-1,3,4-oxadiazol-2-yl)phenyl)-9H-carbazole, and a stir bar were added. The reaction was carried out with reflux for 30 hours. After the completion of reaction, 10% HCl was added and then an extraction was conducted with water and ethyl acetate. The resultant organic layer was concentrated and then purified by column chromatography to obtain a yellow solid product (yield: 77%).

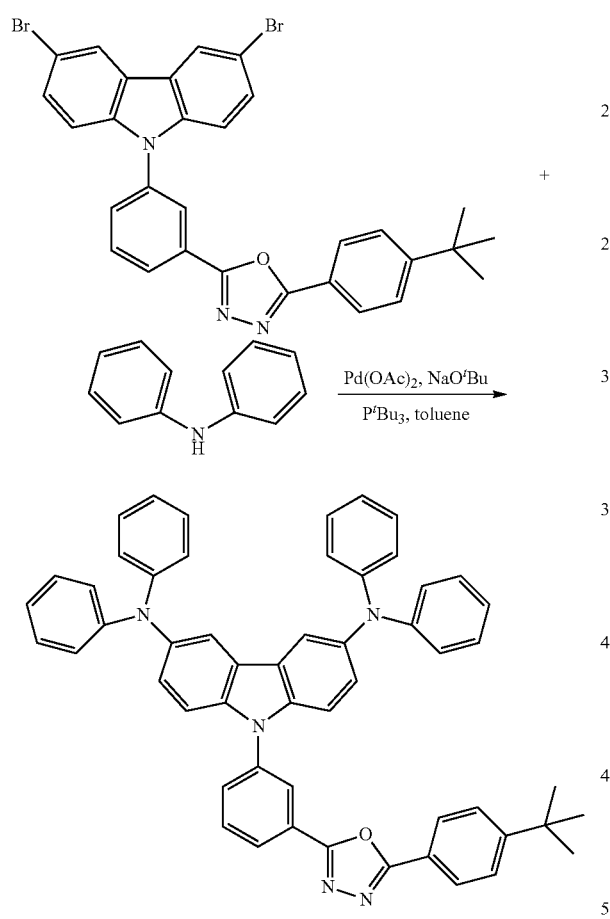

(The Synthesis of Compound 4)

In a 250 ml two-neck flask, 30 ml of toluene, 12 ml of water, 0.5 g (0.4 mmol) of Pd(pph$_3$)$_4$, 3.3 g (24 mmol) of potassium carbonate, 1.5 g (12.3 mmol) of phenylboronic acid, 2 g (4.7 mmol) of 3-(3,6-dibromo-9H-carbazol-9-yl) benzonitrile, 20 ml (1 mmol) of P$^t$Bu$_3$, and a stir bar were added. The reaction was carried out with stirring and reflux under a nitrogen atmosphere for 24 hours. After the completion of reaction, an extraction was conducted with dichloromethane and water, and the resultant organic layer was further concentrated to obtain a solid product, which was purified by column chromatography to obtain a white solid product of 3-(3,6-diphenyl-9H-carbazol-9-yl)benzonitrile (yield: 69.8%).

In a 250 ml two-neck flask, 60 ml of N,N-dimethyl formamide, 450 mg (1.07 mmol) of 3-(3,6-diphenyl-9H-carbazol-9-yl) benzonitrile, 208.71 mg (3.21 mmol) of sodium azide, 171.73 mg (3.21 mmol) of ammonium chloride, and a stir bar were added. The reaction was carried out at a constant temperature of 100° C. under a nitrogen atmosphere for 38 hours. After the completion of reaction, 10 ml of 10% HCl was added and a filtering was conducted. Then an extraction was conducted with ethyl acetate and water. The organic layer was drawn out and dried to obtain a light orange solid product of 3,6-diphenyl-9-(3-2H-tetraazol-5-yl-phenyl)-9H-carbazole (yield: 85%).

In a 250 ml single-neck flask, 100 ml of acetone, 486 mg (1.05 mmol) of 3,6-diphenyl-9-(3-2H-tetraazol-5-yl-phenyl)-9H-carbazole, 149 mg (1.05 mmol) of methyl iodide (CH$_3$I), 145.1 mg (1.05 mmol) of potassium carbonate, and a stir bar were added. After the reaction was carried out with reflux for 18 hours, a filtering was conducted. The crude product was purified by column chromatography to obtain a white solid product (yield: 38%).

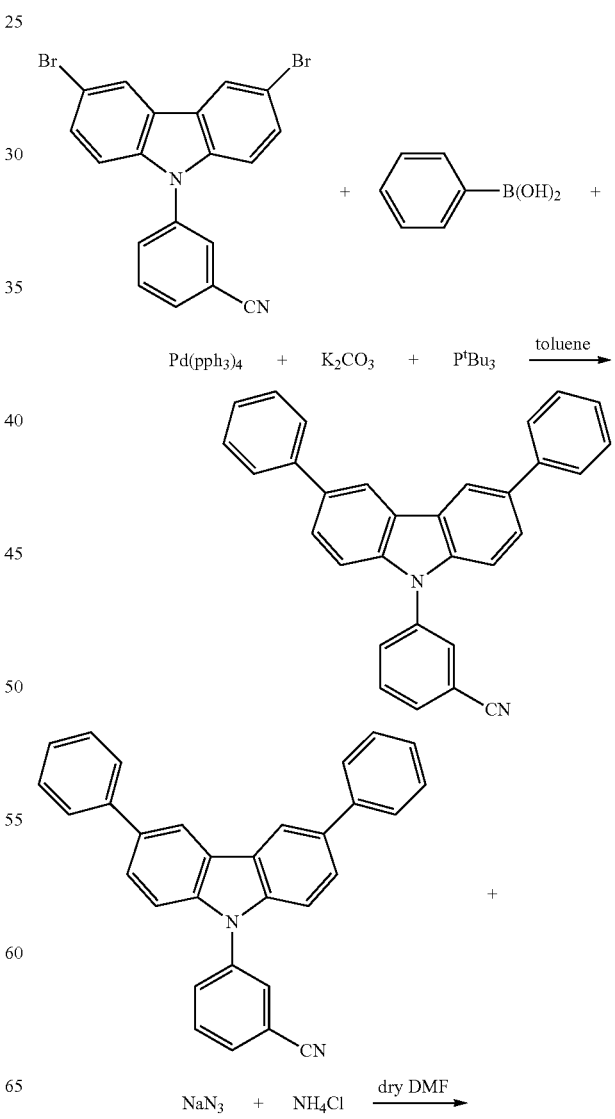

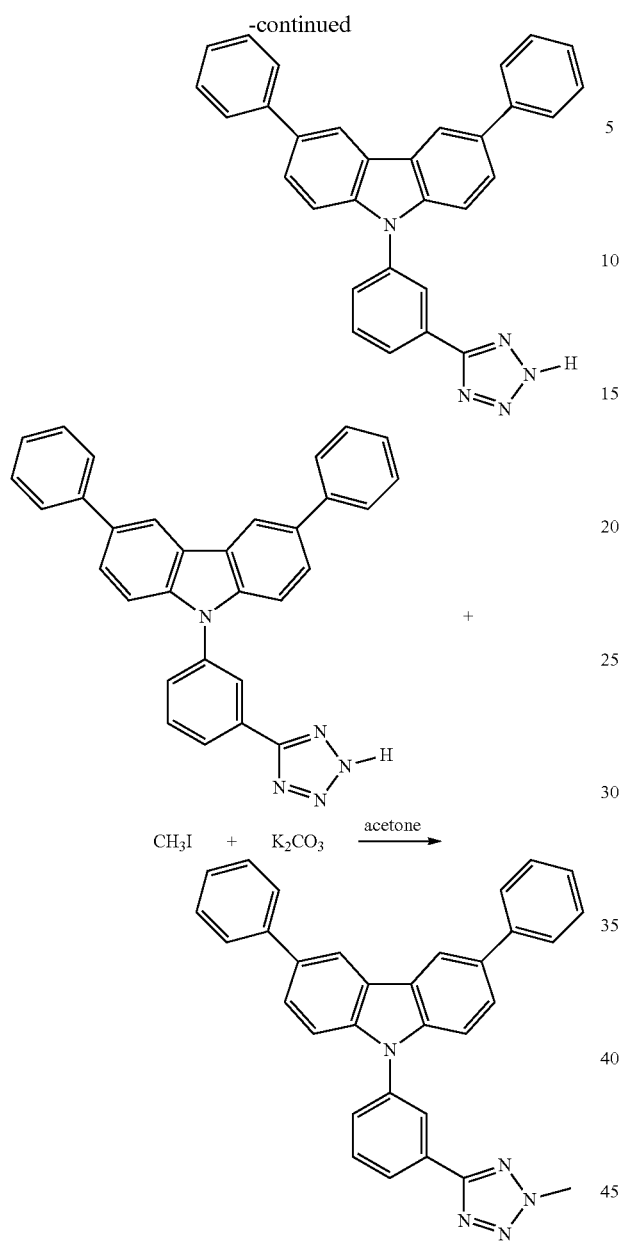
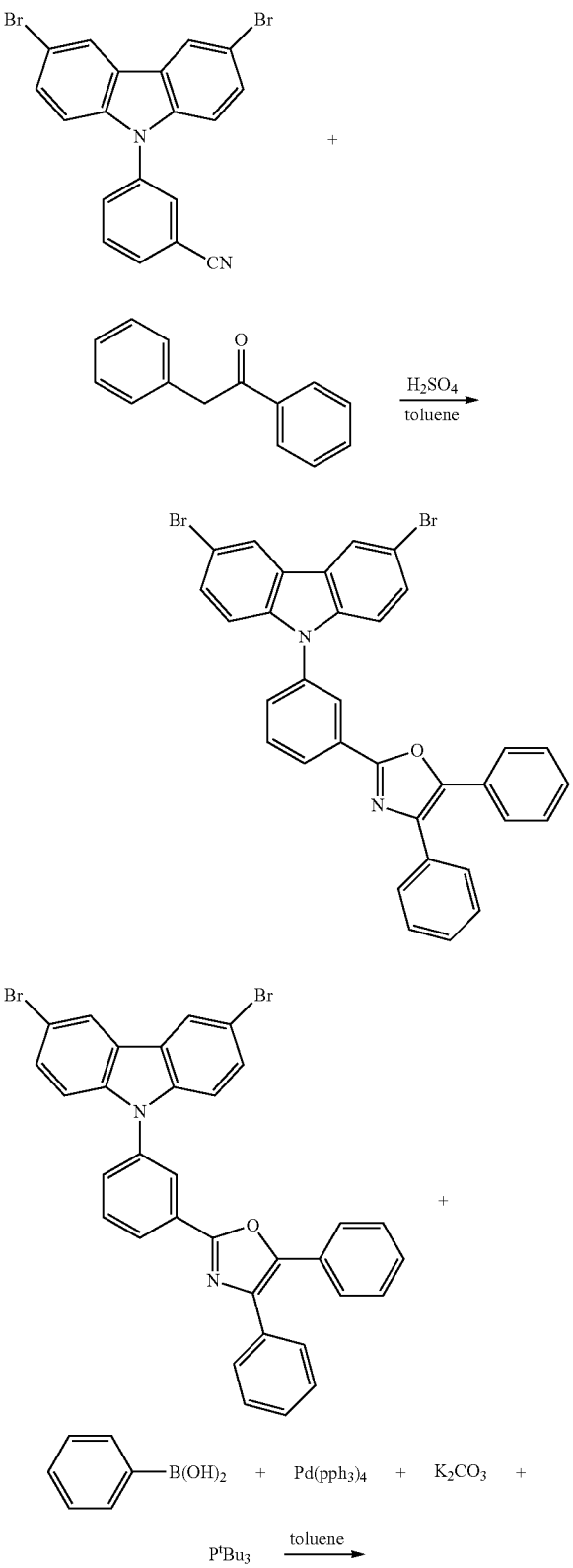

(The Synthesis of Compound 5)

In a 50 ml single-neck flask, 15 ml of toluene, 500 mg (1.17 mmol) of 3-(3,6-dibromo-9H-carbazol-9-yl)benzonitrile, 154 mg (0.785 mmol) of 2-phenylacetophenone, 0.05 ml (0.94 mmol) of concentrated sulfuric acid, and a stir bar were added. After the reaction was carried out with reflux for 24 hours, a filtering was conducted. Then an extraction was conducted with ethyl acetate and water. The crude product was concentrated under a reduced pressure to obtain a white product of 3,6-dibromo-9-3-(4,5-diphenyl-1,3-oxazol-2-yl)-phenyl-9H-carbazole (yield: 77.8%).

In a 50 ml two-neck flask, 15 ml of toluene, 1.9 ml of water, 10.9 mg (0.009 mmol) of Pd(pph$_3$)$_4$, 533 mg (3.8 mmol) of potassium carbonate, 82 mg (0.67 mmol) of phenylboronic acid, 454 mg (0.73 mmol) of 3,6-dibromo-9-3-(4,5-diphenyl-1,3-oxazol-2-yl)-phenyl-9H-carbazole, 0.4 ml (0.02 mmol) of P$^t$Bu$_3$, and a stir bar were added. The reaction was carried out with stirring and reflux under a nitrogen atmosphere for 24 hours. After the completion of reaction, an extraction was conducted with dichloromethane and water, and the resultant organic layer was further concentrated to obtain a solid product, which was purified by column chromatography to obtain a white solid product (yield: 50%).

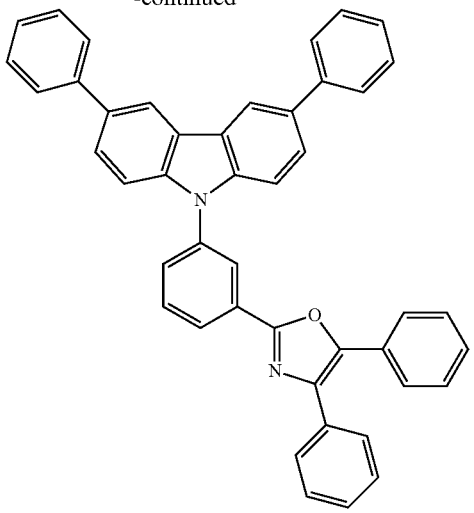

(Examples of Application)

Several examples showing different applications of the OLED devices are provided below, and a test on the properties of these devices was conducted to demonstrate the potentiality of the materials according to the present invention. The test results are shown in Table 1.

Device 1
Anode: an ITO provided on a glass substrate (thickness: 120 nm)
Hole injection layer: PEDOT (Poly(3,4-ethylenedioxythiophene) (4000 rpm)
Hole transporting layer, emitting layer and electron transporting layer: compound 2 (thickness: 100 nm)
Electron injection layer: LiF (thickness: 0.3 nm)
Cathode: Al (thickness: 100 nm)

Device 2
Anode: an ITO provided on a glass substrate (thickness: 120 nm)
Hole transporting layer: compound 2 (thickness: 40 nm)
Emitting layer: tris(2-phenylpyridine) iridium (Ir(ppy)$_3$) as the guest material and compound 2 as the host material (thickness: 30 nm)
Hole blocking layer: 2,9-dimethyl-4,7-diphenyl-1,10-phenanthroline (BCP) (thickness: 10 nm)
Electron transporting layer: Compound 2 (thickness: 20 nm)
Electron injection layer: LiF (thickness: 0.3 nm)
Cathode: Al (thickness: 100 nm)

Device 3
Anode: an ITO provided on a glass substrate (thickness: 120 nm)
Hole injection layer: PEDOT (4000 rpm)
Hole transporting layer: N,N'-bis(naphthalen-1-yl)-N,N'-bis(phenyl)benzidine (NPB) (thickness: 40 nm)
Emitting layer: compound 3 (thickness: 30 nm)
Electron transporting layer: tris(8-hydroxyquinolinato) aluminum (Alq$_3$) (thickness: 30 nm)
Electron injection layer: LiF (thickness: 0.3 nm)
Cathode: Al (thickness: 100 nm)

Device 4
Anode: an ITO provided on a glass substrate (thickness: 120 nm)
Hole transporting layer: NPB (thickness: 40 nm)
Emitting layer: Ir(ppy)$_3$ as the guest material and compound 2 as the host material (thickness: 30 nm)
Hole blocking layer: BCP (thickness: 10 nm)
Electron transporting layer: Alq$_3$ (thickness: 20 nm)
Electron injection layer: LiF (thickness: 0.3 nm)
Cathode: Al (thickness: 100 nm)

TABLE 1

| Device | Operating Voltage (V) | Current (mA) | Luminance (cd/m$^2$) |
|---|---|---|---|
| Device 1 | 12.79 | 57.99 | 30 |
| Device 2 | 12.89 | 0.91 | 1000 |
| Device 3 | 7.31 | 4.31 | 1000 |
| Device 4 | 6.92 | 5.67 | 10000 |

INDUSTRIAL APPLICABILITY

The novel carbazole derivatives of the present invention can be used singly as a hole transporting layer, a host or guest of an emitting layer or an electron transporting layer of an organic light-emitting diode device, and can be used simultaneously as the hole transporting layer, the electron transporting layer and the emitting layer, which can effectively simplify the procedure for manufacture of the devices. Such materials can be used in light-emitting devices such as indicating device, electronic camera, luminescent beam, display, writing beam, reading beam, signal board, optical communication device, illumination device, etc.

What is claimed is:

1. A carbazole derivative having a structure represented by the formula (1):

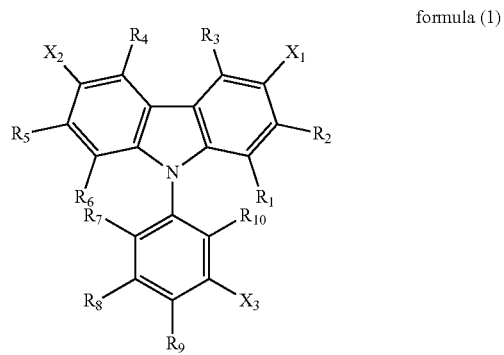

formula (1)

wherein $R_1$-$R_{10}$ are independently selected from the group consisting of hydrogen atom, OH, NH$_2$, NO$_2$, CN, C$_{1-6}$ alkoxyl group, C$_{1-10}$ alkyl group, C$_{1-20}$ fluorinated alkyl group, C$_{2-10}$ alkenyl group, C$_{2-10}$ alkynyl group, C$_{6-20}$ aryl group, C$_{6-20}$ fluorinated aryl group and C$_{4-20}$ heterocyclic aryl group, and X$_1$-X$_2$ are each any one structure selected from the group consisting of the structures represented by the formulae (2)-(3):

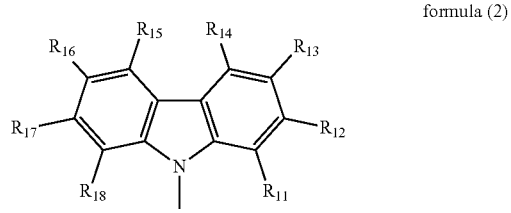

formula (2)

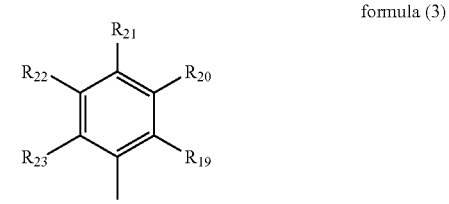

formula (3)

wherein R11-R23 are independently selected from the group consisting of hydrogen atom, OH, NH2, NO2, CN, C1-6 alkoxyl group, C1-10 alkyl group, C2-20 fluorinated alkyl group, C2-10 alkenyl group, C2-10 alkynyl group, C6-20 aryl group, C6-20 fluorinated aryl group and C4-20 heterocyclic aryl group, and X3 is any one structure selected from the group consisting of the structures represented by the formulae (5)-(7):

formula (5)

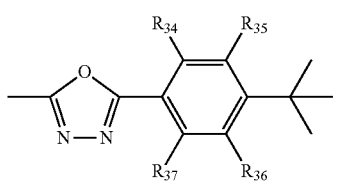

formula (6)

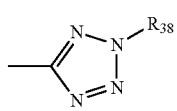

formula (7)

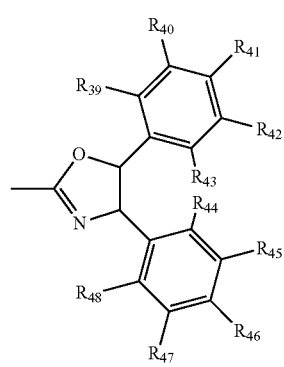

wherein $R_{34}$-$R_{37}$ and $R_{39}$-$R_{48}$ are independently selected from the group consisting of hydrogen atom, OH, NH$_2$, NO$_2$, CN, $C_{1-6}$ alkoxyl group, $C_{1-10}$ alkyl group, $C_{1-20}$ fluorinated alkyl group, $C_{2-10}$ alkenyl group, $C_{2-10}$ alkynyl group, $C_{6-20}$ aryl group, $C_{6-20}$ fluorinated aryl group and $C_{4-20}$ heterocyclic aryl group, and $R_{38}$ is selected from the group consisting of hydrogen atom, $C_{1-4}$ alkyl group and $C_{6-10}$ aryl group.

2. A carbazole derivative according to claim 1, having the following structure when $X_1$ and $X_2$ are carbazol groups and $X_3$ is a 5-(4-tert-butyl-phenyl)-1,3,4-oxadiazol group:

(Compound 1)

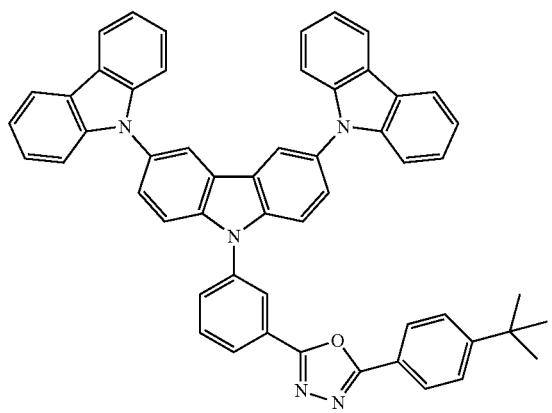

3. A carbazole derivative according to claim 1, having the following structure when $X_1$ and $X_2$ are phenyl groups and $X_3$ is a 5-(4-tert-butyl-phenyl)-1,3,4-oxadiazol group:

(Compound 2)

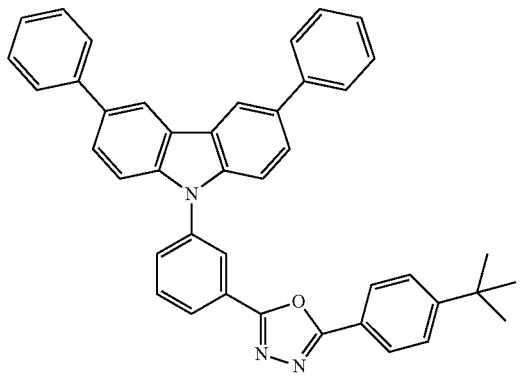

4. A carbazole derivative according to claim 1, having the following structure when $X_1$ and $X_2$ are phenyl groups and $X_3$ is a 2-methyl-1H-tetraazol-5-yl group:

(Compound 4)

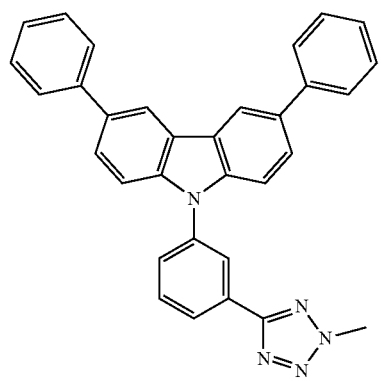

5. A carbazole derivative according to claim 1, having the following structure when $X_1$ and $X_2$ are phenyl groups and $X_3$ is a 4,5-diphenyl-1,3-oxazol-2-yl group:

(Compound 5)

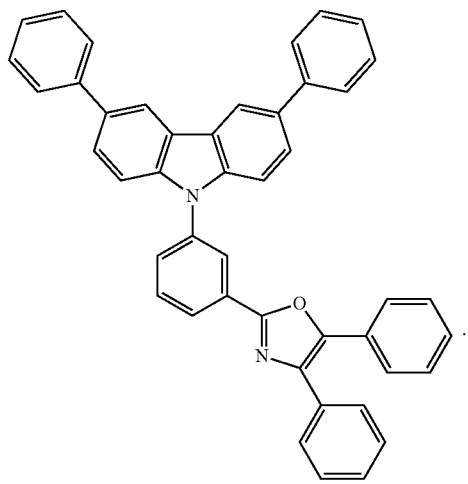

6. An organic light-emitting diode device, characterized by containing a carbazole derivative according to claim 1 between a pair of electrodes, wherein the carbazole derivative is used as a material for a hole transporting layer, an electron transporting layer, or a host or guest of an emitting layer of the organic light-emitting diode device.

7. An organic light-emitting diode device, characterized by containing a carbazole derivative according to claim 2 between a pair of electrodes, wherein the carbazole derivative is used as a material for a hole transporting layer, an electron transporting layer, or a host or guest of an emitting layer of the organic light-emitting diode device.

8. An organic light-emitting diode device, characterized by containing a carbazole derivative according to claim 3 between a pair of electrodes, wherein the carbazole derivative is used as a material for a hole transporting layer, an electron transporting layer, or a host or guest of an emitting layer of the organic light-emitting diode device.

9. An organic light-emitting diode device, characterized by containing a carbazole derivative according to claim 4 between a pair of electrodes, wherein the carbazole derivative is used as a material for a hole transporting layer, an electron transporting layer, or a host or guest of an emitting layer of the organic light-emitting diode device.

10. An organic light-emitting diode device, characterized by containing a carbazole derivative according to claim 5 between a pair of electrodes, wherein the carbazole derivative is used as a material for a hole transporting layer, an electron transporting layer, or a host or guest of an emitting layer of the organic light-emitting diode device.

\* \* \* \* \*

UNITED STATES PATENT AND TRADEMARK OFFICE
CERTIFICATE OF CORRECTION

| | | |
|---|---|---|
| PATENT NO. | : 8,859,113 B2 | Page 1 of 1 |
| APPLICATION NO. | : 14/048558 | |
| DATED | : October 14, 2014 | |
| INVENTOR(S) | : Hsiao Chan Liu et al. | |

It is certified that error appears in the above-identified patent and that said Letters Patent is hereby corrected as shown below:

On the title page, item (72), please change the first Inventor's name to "Hsiao Chan Liu".

Signed and Sealed this
Sixth Day of January, 2015

Michelle K. Lee
*Deputy Director of the United States Patent and Trademark Office*